[19] United States Patent
Behre et al.

[11] Patent Number: 4,540,817
[45] Date of Patent: Sep. 10, 1985

[54] PROCESS FOR THE PREPARATION OF 5-AMINO-2,4-DIMETHYLACETANILIDE

[75] Inventors: Horst Behre; Heinz U. Blank, both of Odenthal; Alfred Seyberlich; Ferdinand Hagedorn, both of Leverkusen, all of Fed. Rep. of Germany

[73] Assignee: Bayer Aktiengesellschaft, Leverkusen, Fed. Rep. of Germany

[21] Appl. No.: 516,438

[22] Filed: Jul. 25, 1983

Related U.S. Application Data

[63] Continuation of Ser. No. 326,648, Dec. 2, 1981, abandoned.

[30] Foreign Application Priority Data

Dec. 19, 1980 [DE] Fed. Rep. of Germany ....... 3047946

[51] Int. Cl.$^3$ ............................................ C07C 102/00
[52] U.S. Cl. .................................... 564/218; 564/146; 564/219; 564/414; 564/419; 564/422; 564/437; 564/441
[58] Field of Search ................. 564/218, 219, 146, 437

[56] References Cited

U.S. PATENT DOCUMENTS 1,920,828  8/1933  Wyler ............................ 564/146 X
2,933,503  4/1960  Clark et al. ..................... 564/218 X
3,149,162  9/1964  Gardner et al. ................... 564/437
3,654,363  4/1972  Pum et al. ....................... 564/218 X
4,009,205  2/1977  Kimura et al. ................... 564/218 X
4,341,902  7/1982  Thiem et al. ....................... 564/218

FOREIGN PATENT DOCUMENTS 1643264  6/1971  Fed. Rep. of Germany .

OTHER PUBLICATIONS

Beilsteine, "Handbuch der Organischen Chem.", vol. XII, pp. 1127–1129, (1929).

Primary Examiner—Robert V. Hines
Attorney, Agent, or Firm—Sprung Horn Kramer & Woods

[57] ABSTRACT

A process for the preparation of 5-amino-2,4-dimethylacetanilide by reduction of 5-nitro-2,4-dimethylacetanilide with hydrogen is disclosed characterized in that a crude mixture containing 5-nitro-2,4-dimethylacetanilide in admixture with at least one of its position isomers is hydrogenated in a water-miscible organic solvent which optionally contains water. The 5-amino-2,4-dimethylacetanilide is separated off from the reaction mixture by means of crystallization employing a mixture of water-miscible organic solvent and water.

15 Claims, No Drawings

PROCESS FOR THE PREPARATION OF 5-AMINO-2,4-DIMETHYLACETANILIDE

This application is a continuation of application Ser. No. 326,648, filed Dec. 2, 1981, and now abandoned.

The present invention relates to a process for the preparation of 5-amino-2,4-dimethylacetanilide by catalytic hydrogenation of a crude nitration mixture, which contains the various isomeric mononitro-2,4-dimethylacetanilides.

The 5-amino-2,4-dimethylacetanilide is described in the literature, and is of interest, for example, as an intermediate product for the preparation of the plant protecting agent 5-acetamido-2,4-dimethyltrifluoromethanesulphonanilide German Offenlegungsschrift 2,406,475, German Offenlegungsschrift 2,412,578 and U.S. Pat. No. 4,013,444).

The preparation of the 5-amino-2,4-dimethylacetanilide, starting from 2,4-dimethylaniline (2,4-xylidine), can be effected, for example, in the following manner:

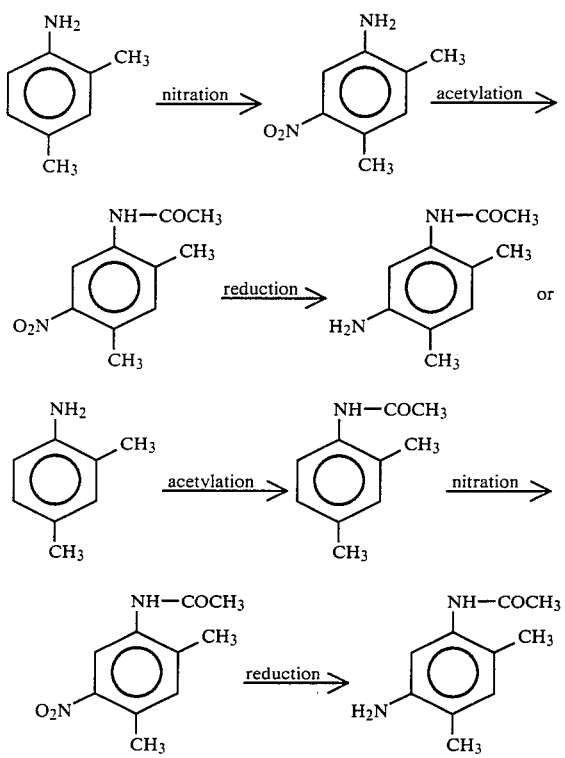

The two nitration steps appearing in the equations through nitration with nitric acid in concentrated sulphuric acid, and the acetylation, are described in the literature (Beilsteins Handbuch der organischen Chemie, Hauptwerk (Beilsteins Handbook of Organic Chemistry, Main Work), 4th Edition 1929, Volume XII, page 1129). By both described routes, the 5-nitro-2,4-dimethylacetanilide is not precipitated in pure form on introducing the nitration mixture into water, but as a mixture with the isomeric 3-nitro-compound and 6-nitro-compound. In addition, the desired 5-nitro-compound can be contaminated in small amounts with dinitro-compounds and with further by-products of unknown structure in varying amounts. A complicated process of dissolution and crystallization from organic solvents is therefore necessary for the purification of the desired 5-nitro-compound, entailing losses of material and solvents as well as a considerable investment of labour.

Further, the reduction of the 5-nitro-2,4-dimethylacetanilide with zinc dust and ammonium chloride in boiling aqueous ethanol (50% by weight) to give 5-amino-2,4-dimethylacetanilide is known (J. Chem. Soc. 119, 717 to 721 (1921)). However, this reduction method is too complicated for an industrial process and is therefore not suitable.

A process for the preparation of 5-amino-2,4-dimethylacetanilide from 5-nitro-2,4-dimethylacetanilide by reduction has now been found, which is characterized in that a mixture containing the isomeric mononitro-2,4-dimethylacetanilides, with a content of 60 to 95% by weight of 5-nitro-2,4-dimethylacetanilide, relative to the total weight of this mixture, is treated with hydrogen over a hydrogenation catalyst under hydrogenation conditions in a water-miscible organic solvent, which is suitable for this reaction and which optionally contains water, the hydrogenation catalyst is separated off, and the 5-amino-2,4-dimethylacetanilide formed is separated from a mixture of the water-miscible organic solvent and water by means of crystallization.

The mixture to be employed according to the invention, containing the isomeric mononitro-2,4-dimethylacetanilides, can be prepared, for example, according to one of the routes characterized above by the equations. In this process, for example, the nitration mixture is introduced into excess water after the particular nitration step has ended, so that the organic material is to a large extent isolated from the nitration mixture by precipitation, and the mixture, to be employed according to the invention, of the isomeric compounds is formed. In the case in which the nitration step is carried out before the acetylation, the mixture just described, which has formed in the nitration, is subjected to the acetylation without working-up. The lower limit for the content of desired 5-nitro-2,4-dimethylacetanilide is, for example, about 60% by weight, relative to the total mixture, preferably about 70% by weight, and particularly preferably about 75% by weight. The upper limit of the content of desired 5-nitro-2,4-dimethylacetanilide in the mixture to be employed according to the invention is, for example, about 95% by weight, relative to the total weight of this mixture, preferably about 93% by weight, and particularly preferably about 90% by weight. Of course, mixtures in which the 5-nitro-2,4-dimethylacetanilide is present in a higher degree of purity can also be reacted according to the invention. Of course, mixtures of the isomeric mononitro-2,4-dimethylacetanilides which have been obtained by a route other than that indicated can, furthermore, be reacted according to the invention. Furthermore, such mixtures to be employed according to the invention can contain, for example, 0.1 to 5% by weight, relative to the sum of the 3 isomeric mononitro-compounds mentioned, of unknown compounds. Furthermore, such mixtures can be employed as dried goods or, preferably, as goods which are damp with water, for example with a water content of up to about 50% by weight. In addition, they can contain small amounts of residual chemicals from the previous reaction steps described above by way of example, for example sulphuric acid and/or inorganic salts such as sodium sulphate.

A mixture in which the isomeric mononitro-compounds, without mentioning possibly present further accompanying substances, are present within the following limits may be mentioned as an example of a typical mixture which can be employed according to the invention: 75 to 94.9% by weight of 5-nitro-compound, 5 to 20% by weight of 3-nitro-compound and 0.1 to 10% by weight of 6-nitro-compound.

The process according to the invention is carried out in a water-miscible organic solvent which is suitable for the catalytic hydrogenation and which optionally contains water. In this respect, those solvents may be designated as being suitable which are unchanged or only changed to a limited extent, for example in a quantity of less than 2%, relative to the quantity of solvent employed, under the hydrogenation conditions, or which undergo changes, for example by hydrogenation, which in turn lead to suitable compounds. Lower aliphatic alcohols with, for example, 1 to 6 C atoms, such as methanol, ethanol, propanol, isopropanol, butanol or hexanol, water-miscible ethers, such as tetrahydrofuran or dioxane, or lower aliphatic amines, such as trimethylamine, ethylamine, diethylamine, triethylamine, propylamine or ethylenediamine, and amides preferably substituted on the N-atom, such as formamide, dimethylformamide or dimethylacetamide, may be mentioned as examples for this process. Among the compounds mentioned, lower aliphatic alcohols are preferred, particularly those with 1 to 4 C atoms, and methanol is very particularly preferred. These solvents can be used in pure form as well as in mixtures with water. For example, ratios by weight of organic solvent to water such as 100:1 to 1:100, preferably 100:1 to 1:10, are suitable mixing ratios.

In the process according to the invention, a concentration of the mixture of the isomeric mononitro-2,4-dimethylacetanilide, in the solution or suspension to be hydrogenated, of 5 to 40% by weight, preferably 10 to 35% by weight, particularly preferably 15 to 30% by weight, relative to the weight of the total hydrogenation mixture, is established.

The process according to the invention is carried out over a hydrogenation catalyst. Examples of such catalysts which may be mentioned are Raney nickel catalysts which contain nickel as the active component, alone or alloyed, for example with one or several of the following metals: molybdenum, titanium, vanadium, magnesium, iron, cobalt and chromium; in addition, residual aluminium from the preparation of the Raney catalyst can be present. Furthermore, noble metal catalysts which contain one or several of the metals osmium, iridium, platinum, ruthenium, rhodium and palladium may be mentioned as examples. Such noble metal catalysts can be employed with or without carrier material. In the case in which a carrier material is employed, carbonates and sulphates of the alkaline earth metals, such as barium carbonate, barium sulphate, calcium carbonate and calcium sulphate, or alumina, aluminum oxide, silicon dioxide and silicic acids, as well as charcoal, particularly in the form of active charcoal, may be mentioned as examples. Furthermore, sulphide hydrogenation catalysts, such as cobalt sulphide, may be mentioned for use in the process according to the invention. Among the hydrogenation catalysts which can be employed according to the invention, Raney catalysts may be preferably mentioned, and among these, Rancy nickel may be preferably mentioned.

The quantity of the hydrogenation catalyst for the process according to the invention is, for example, 0.5 to 8% by weight, preferably 2 to 5% by weight, relative to the total weight of the reaction mixture. These data refer to the dry weight of the catalyst. In the case in which hydrogenation catalysts, such as Raney catalysts, must be stored under water because of their pyrophoric properties, double the quantity given above must be employed, for example, in the case of a Raney catalyst containing 50% by weight of water. The water content of such a catalyst interferes in this process just as little as a possible water content of the mixture of the mononitro-compounds, since, as already stated, the process according to the invention can be optionally carried out, in a preferred embodiment, in an organic solvent which contains water. The process according to the invention can, of course, also be carried out with an input of catalyst higher than that indicated. However, no particular advantages result therefrom, so that additional catalyst is less preferable from economic considerations.

The hydrogenation catalyst can be repeatedly used in the process according to the invention. In this process, the activity of the hydrogenation catalyst is to a large extent or even completely retained. This is extraordinarily surprising, since impure starting substances, such as the mixtures to be employed according to the invention, always involve the danger of catalyst poisoning, particularly if they still contain unknown compounds. This fact, generally known to the expert from the field of active hydrogenation catalysts, is not observed in the process according to the invention. In the case in which a relatively large number of reaction runs are carried out with repeated use of the hydrogenation catalyst, for example more than 10 or 20, it can be propitious, however, to remove a small amount of the hydrogenation catalyst recovered and to replace it by fresh catalyst, as a precaution after every reaction run. 0.01 to 4% by weight, preferably 0.05 to 2% by weight, relative to the weight of the recovered catalyst, may be mentioned as examples of such a small amount to be removed. These extremely small consumptions of catalyst represent a particularly favourable economic aspect of the process according to the invention.

The hydrogenation can be carried out, for example, at a temperature of from 20° to 200° C., preferably 40° to 120° C., and under a hydrogen pressure of, for example, 1 to 200 bars, preferably 3 to 50 bars, particularly preferably 5 to 25 bars.

It is an essential characteristic of the process according to the invention that the 5-amino-2,4-dimethylacetanilide formed by hydrogenation is separated from the undesired accompanying substances by crystallization from a mixture of the water-miscible organic solvent and water. This is surprising, since it is known that crystallizations of organic compounds from a mixture containing water, particularly from a water-rich mixture, often lead to coprecipitations. Also surprising is the fact that, among the undesired isomers, even the very poorly soluble 6-amino-isomer remains in the mother liquor of the crystallization process and makes possible the recovery of a pure 5-amino-2,4-dimethylacetanilide with a purity of 99.5 to 99.9% by weight, relative to the total reaction product obtained as crystals. In the mixture of the water-miscible organic solvent and water, which is used for the crystallization, the water is present in a quantity of at least about 50% by weight, relative to the total solution mixture, for example in a quantity of about 50 to about 95% by weight. In the large range of variation of the process according to the invention with respect to the type of water-miscible organic solvent to be employed and with respect to the variable composition of the crude nitration mixture to be employed, the optimum water content for the crystallization mixture can be determined for each combination of such a water/solvent mixture and the crude nitration mixture by simple preliminary experiments. A water/alcohol ratio by weight in the range of 2:1 to 20:1, preferably 3:1 to 10:1, may be given as an example for the lower aliphatic alcohols to be preferably employed, in particular for methanol. For the crude mononitro-2,4-dimethylacetanilide mixtures which are particularly preferably to be employed and which have been described above, good results are obtained, for example, if the 5-amino-2,4-dimethylacetanilide is crystallized from a water/methanol mixture in the ratio by weight of about 3:1 to 10:1. For this purpose, about 3 to 20, preferably 5 to 15, parts by weight of such a water/methanol mixture are required per 1 part by weight of 5-amino-2,4-dimethylacetanilide.

To establish such a favourable water/solvent ratio by weight in connection with the favourable substrate/solvent mixture for the hydrogenation, described above, it can be necessary, after the hydrogenation and after the separation of the hydrogenation catalyst, for example by filtration or centrifuging, to remove a part of the water-miscible solvent present in the hydrogenation mixture, for example methanol, by means of distillation; in the case in which the hydrogenation mixture contains water, a part of this water can also distil off during this distillation. In this process, a concentrated organic or organic-aqueous, for example methanolic or methanolicaqueous, solution or suspension of a monoamino-2,4-dimethylacetanilide mixture is obtained as the distillation residue, which can directly be brought by cooling to crystallization or further crystallization or is brought to crystallization after previous addition of water or, if appropriate, of further organic solvent, for example methanol, to establish the optimum substrate-dependent and solvent-dependent solvent quantities listed above. The addition of water (or, more rarely, of an organic solvent) can, however, also be effected in the hydrogenation mixture which has been freed from hydrogenation catalyst, before a distillative separation of the solvent, or, in rarer cases, of the water, is effected. This latter case can, for example, be advantageous if the hydrogenation has been carried out in methanol or in an aqueous methanol with, for example, 10 to 50% by weight of water content, relative to the methanol/water mixture. In such a case, finally, the water (or in rarer cases the organic solvent) can be added to the mixture during such a distillation, in an even further variant.

Furthermore, it is possible within the scope of the process according to the invention already to establish such a water/solvent ratio by weight for the hydrogenation as is to be provided for the subsequent crystallisation of the desired amino-compound obtained by hydrogenation.

A temperature of, for example, 0° to 60° C., preferably 5° to 30° C., is established for the crystallization of the 5-amino-2,4-dimethylacetanilide.

The process according to the invention has the following essential advantages in comparison with the processes known from the literature:

1. Use of an industrial mononitro-2,4-dimethylacetanilide isomer mixture, whereby a complicated purification of the desired 5-nitro-2,4-dimethylacetanilide in a purification operation, for example by recrystallisation from organic solvents, which is associated with losses in yield, can be avoided.

2. Carrying out the reduction step as a catalytic hydrogenation in contrast to the reduction processes with zinc and ammonium chloride, which are known from the literature. This reduction over hydrogenation catalysts can, surprisingly, be carried out without signs of poisoning or of exhaustion of this catalyst and is therefore extremely economical, since only very little fresh catalyst is needed for the hydrogenation and high space/time yields can be achieved in the solvent/water mixture as the hydrogenation medium.

3. Isolation of the 5-amino-2,4-dimethylacetanilide in a very simple and economical manner by using crystallization mixtures with a high water content. Surprisingly, high purities are obtained in this process, although the necessity of organic crystallization media and a repeated performance of the crystallization process may be expected from the presence of compounds in the reaction mixture which are soluble with difficulty, such as the 6-amino-isomer and perhaps unchanged nitro compounds.

EXAMPLE 1

200 g of mononitro-2,4-dimethylacetanilide isomer mixture of the following composition: 77% by weight of 5-nitro-2,4-dimethylacetanilide, 14% by weight of 3-nitro-2,4-dimethylacetanilide, 6% by weight of 6-nitro-2,4-dimethylacetanilide, 2.5% by weight of unknown contaminants and 0.5% by weight of water, and 635 g of methanol and 40 g of Raney nickel, 100% strength, are employed in a 2.7 l hydrogenation autoclave.

The reaction mixture is hydrogenated at 80° C. and under a hydrogen pressure of 20 bars in the course of 30 minutes, and is further stirred for 30 minutes at 80° C. after the absorption of hydrogen has ended. The catalyst is filtered off whilst hot and is washed with 80 g of methanol. 475 g of methanol is distilled off from the filtrate under normal pressure over a column. The hot residual solution from the distillation is allowed to run into 1,500 g of water, whilst stirring. The reaction mixture is stirred until it has cooled to 20° C., and is further stirred for 1 hour at this temperature. The precipitated product is filtered off, and is washed with twice 200 g of cold water and dried at 60° C. in vacuo. Yield 110 g of dry product with a melting point of 162° to 163° C., corresponding to a yield of 84% of the theoretical yield, relative to the content of 5-nitro-2,4-dimethylacetanilide in the mononitro-2,4-dimethylacetanilide isomer mixture employed.

The following contents have been determined in the isolated product by means of diazotisation and thin layer chromatography: 99.5% by weight of 5-amino-2,4-dimethylacetanilide, 0.2% by weight of 3-amino-2,4-dimethylacetanilide, 0.1% by weight of 6-amino-2,4-dimethylacetanilide and 0.2% by weight of unknown compounds.

EXAMPLE 2

A hydrogenation as carried out in Example 1, but at a temperature of 70° C. and under a hydrogen pressure of 10 bars, leads to a yield of 86% of the theoretical yield, relative to the content of 5-nitro-2,4-dimethylacetanilide in the mononitro-2,4-dimethylacetanilide isomer mixture employed.

EXAMPLE 3

230 g of mononitro-2,4-dimethylacetanilide isomer mixture which is moist with water (corresponding to 160 g of dry product) of the following composition, relative to dry substance: 90.2% by weight of 5-nitro-2,4-dimethylacetanilide, 9.5% by weight of 3-nitro-2,4-dimethylacetanilide and 0.3% by weight of 6-nitro-2,4-dimethylacetanilide, and 792 g of methanol and 30 g of Raney nickel, 100% strength, are employed in a 2.7 l hydrogenation autoclave. The reaction mixture is hydrogenated at 80° C. and under a hydrogen pressure of 10 bars in the course of 1 hour, and is further stirred for 30 minutes at 80° C. after the absorption of hydrogen has ended. The catalyst is filtered off whilst hot and is washed with 40 g of methanol. 600 g of methanol is distilled off from the filtrate under normal pressure over a column. The hot residual solution from the distillation is allowed to run into 1,000 g of water, whilst stirring. The reaction mixture is cooled to 20° C., whilst stirring, and the precipitated product is filtered, washed in turn with 150 g of water at 20° C. and 150 g of water at 0° C. and dried at 60° C. in vacuo. Yield 107 g of dry product with a melting point of 165° to 166° C., corresponding to a yield of 86% of the theoretical yield, relative to the content of 5-nitro-2,4-dimethylacetanilide in the mononitro-2,4-dimethylacetanilide isomer mixture employed.

The following contents have been determined in the isolated product by means of diazotization and thin layer chromatography: 99.9% by weight of 5-amino-2,4-dimethylacetanilide and 0.1% by weight of unknown compound.

EXAMPLE 3a

Preparation of the mononitro-2,4-dimethylacetanilide isomer mixture 300 g (5.0 mols) of glacial acetic acid are initially introduced into a 1 l four-necked flask with a stirrer, condenser, dropping funnel and internal thermometer. 141 g of mononitro-2,4-dimethylaniline isomer mixture (prepared by nitration of 121 g=1.0 mol of 2,4-dimethylaniline) of the following composition: 90.2% by weight of 5-nitro-2,4-dimethylaniline, 9.5% by weight of 3-nitro-2,4-dimethylaniline, and 0.3% by weight of 6-nitro-2,4-dimethylaniline are introduced into the flask at 20° C. 122 g (1.2 mols) of acetic anhydride are added dropwise to the mixture in the course of 1 hour, whilst cooling, and the temperature is not to rise above 55° C. The reaction mixture is then heated to boiling and is heated under reflux for 1 hour. 300 g is glacial acetic acid are then distilled off under normal pressure. The approximately 120° C. hot reaction solution is allowed to run into an initially introduced quantity of 1,500 g of water at 35° C., whilst stirring, and the temperature is not to rise above 60° C. The reaction mixture is cooled to 20° C., whilst stirring, and the precipitated product is filtered, washed with water until free from acetic acid and dried well under suction. Yield about 230 g of moist product with the relative composition given above.

EXAMPLE 4

A hydrogenation carried out as in Example 3, but with a 15-fold re-use of the used Raney nickel catalyst, led to a yield of 84% of theory. An extension of the hydrogenation time was not necessary.

EXAMPLE 5

A hydrogenation carried out as in Example 3, but with 400 g of methanol and 400 g of water at 60° C. and a hydrogen pressure of 15 bars, led to a yield of 86% of the theoretical yield, after 300 g of methanol had been distilled off and 600 g of water added.

EXAMPLE 6

A hydrogenation carried out as in Example 1, but in 235 g of methanol and 1,200 g of water at 60° C. and under a hydrogen pressure of 10 bars, led, without distilling off methanol and without addition of water, to a yield of 90%, relative to the content of 5-nitro-2,4-dimethylacetanilide in the mononitro-2,4-dimethylacetanilide isomer mixture employed. The following contents have been determined in the isolated product by means of diazotization and thin layer chromatography: 99.7% by weight of 5-amino-2,4-dimethylacetanilide, 0.2% by weight of 3-amino-2,4-dimethylacetanilide, 0.0% by weight of 6-amino-2,4-dimethylacetanilide and 0.1% by weight of unknown compounds.

What is claimed is:

1. A process for the preparation of 5-amino-2,4-dimethylacetanilide which comprises contacting 5-nitro-2,4-dimethylacetanilide in the form of a mixture containing 70 to 94.9% by weight of 5-nitro-2,4-dimethylacetanilide, 5 to 20% by weight of 3-nitro-2,4-dimethylacetanilide and 0.1 to 10% by weight of 6-nitro-2,4-dimethylacetanilide, relative to the sum of said compounds with hydrogen in the presence of a hydrogenation catalyst under hydrogenation conditions in a mixture of water and an alkanol wherein these solvents are present in a 100:1 to 1:100 weight ratio, separating off the hydrogenation catalysts and separating 5-amino-2,4-dimethylacetanilide from a mixture of alkanol and water by means of crystallization.

2. A process according to claim 1, wherein said alkanol is a lower aliphatic alcohol.

3. A process according to 1, wherein said alkanol is methanol.

4. A process according to claim 1, wherein the hydrogenation catalyst is employed in an amount of from 0.5 to 8% by weight relative to the amount of the reaction mixture.

5. A process according to claim 1, wherein the hydrogenation catalyst is Raney nickel.

6. A process according to claim 1, wherein crystallization of the 5-amino-2,4-dimethylacetanilide is carried out in a water/alkanol mixture having a weight ratio of water to alcohol of 2-20:1.

7. A process according to claim 6, wherein the crystallization is carried out in a water/methanol mixture with a weight ratio of water to methanol of 3-10:1 and a proportion of 3 to 20 parts by weight of such water/methanol mixture to one part by weight of isolated 5-amino-2,4-dimethylacetanilide.

8. A process according to claim 1, wherein crystallization is effected at a temperature of between 0° and 60° C.

9. A process according to claim 1, wherein following the hydrogenation, alkanol is removed and thereafter water is added to the reaction product.

10. A process according to claim 9, wherein said alkanol is methanol.

11. A process according to claim 10, wherein additional methanol is added to the reaction product before said alkanol is removed.

12. A process according to claim 11, wherein said alkanol is removed by distillation.

13. A process according to claim 9, wherein a mixture of methanol and water containing 10 to 50% by weight water is employed for said crystallization.

14. A process for the preparation of 5-amino-2,4-dimethylacetanilide which comprises:
   (A) contacting 2,4-dimethylaniline with nitric acid in concentrated sulphuric acid under nitration conditions whereby to form the corresponding 5-nitro compound in a mixture with at lest one of the corresponding 3-nitro and 6-nitro compounds;
   (B) contacting the mixture of nitro-2,4-dimethylanilide obtained from step A with an acetylating agent whereby to form a mixture of 5-nitro-2,4-dimethylacetanilide containing 70 to 94.9% by weight of 5-nitro-2,4-dimethylacetanilide, 5 to 20% by weight of 3-nitro-2,4-dimethylacetanilide and 0.1 to 10% by weight of 6-nitro-2,4-dimethylacetanilide, relative to the sum of said compounds; and
   (C) contacting the mixture of nitro-2,4-dimethylacetanilides of step B with hydrogen in the presence of a hydrogenation catalyst under hydrogenation conditions in a mixture of water and an alkanol, separating off the hydrogenated catalyst and separating 5-amino-2,4-dimethylacetanilide from a mixture of alkanol and water by means of crystallization.

15. A process according to claim 14 wherein said 5-amino-2,4,-dimethylacetanilide is separated from a mixture of water and methanol.

* * * * *